United States Patent
Elliott et al.

[11] Patent Number: 6,074,996
[45] Date of Patent: *Jun. 13, 2000

[54] LIQUID PERSONAL CLEANSING COMPOSITION CONTAINING CATIONIC POLYMERIC SKIN CONDITIONING AGENT

[75] Inventors: Russell Phillip Elliott, Surrey; Matthew Thomas Green, Middlesex; Christopher David Leahy, Surrey, all of United Kingdom

[73] Assignee: The Procter & Gamble Company, Cincinnati, Ohio

[ * ] Notice: This patent is subject to a terminal disclaimer.

[21] Appl. No.: 08/973,050

[22] PCT Filed: May 9, 1996

[86] PCT No.: PCT/US96/06577

§ 371 Date: Nov. 26, 1997

§ 102(e) Date: Nov. 26, 1997

[87] PCT Pub. No.: WO96/37588

PCT Pub. Date: Nov. 28, 1996

[30] Foreign Application Priority Data

May 27, 1995 [GB] United Kingdom ............... 9510838

[51] Int. Cl.$^7$ .................. C11D 1/12; C11D 1/83; C11D 1/835; C11D 1/94

[52] U.S. Cl. ............ 510/125; 510/123; 510/124; 510/126; 510/127; 510/137; 510/138; 510/158; 510/159; 510/504; 424/70.12; 424/70.13; 424/70.16; 424/70.19; 424/70.21; 424/70.22; 424/70.24; 424/70.31; 514/846

[58] Field of Search ............... 510/123, 124, 510/125, 126, 127, 137, 138, 158, 159, 504; 424/70.12, 70.13, 70.16, 70.19, 70.21, 70.22, 70.24, 70.31; 514/846

[56] References Cited

U.S. PATENT DOCUMENTS

| | | | |
|---|---|---|---|
| 4,368,213 | 1/1983 | Hollenbach et al. | 426/590 |
| 4,435,317 | 3/1984 | Gerritsen et al. | 252/547 |
| 4,446,165 | 5/1984 | Roberts | 426/602 |
| 4,731,201 | 3/1988 | Robbins et al. | 252/551 |
| 4,740,367 | 4/1988 | Force et al. | 424/47 |
| 4,857,213 | 8/1989 | Caswell et al. | 252/8.75 |
| 4,997,641 | 3/1991 | Hartnett et al. | 424/70 |
| 5,078,990 | 1/1992 | Martin et al. | 424/70 |
| 5,106,613 | 4/1992 | Hartnett et al. | 424/71 |
| 5,120,532 | 6/1992 | Wells et al. | 424/70 |
| 5,152,914 | 10/1992 | Forster et al. | 252/174 |
| 5,160,738 | 11/1992 | Macaulay et al. | 424/401 |
| 5,213,716 | 5/1993 | Patel et al. | 252/547 |
| 5,302,322 | 4/1994 | Birtwistle | 252/847 |
| 5,318,728 | 6/1994 | Surutzidis et al. | 252/548 |
| 5,332,528 | 7/1994 | Pan et al. | 252/548 |
| 5,348,736 | 9/1994 | Patel et al. | 424/70 |
| 5,357,667 | 10/1994 | Bergmann | 252/547 |
| 5,395,542 | 3/1995 | Nozaki et al. | 252/174.16 |
| 5,409,640 | 4/1995 | Giret et al. | 252/546 |
| 5,417,893 | 5/1995 | Ofosu-Asante | 252/558 |
| 5,439,615 | 8/1995 | Lefebvre et al. | 252/548 |
| 5,439,682 | 8/1995 | Wivell et al. | 724/401 |
| 5,585,104 | 12/1996 | Ha et al. | 424/401 |

OTHER PUBLICATIONS

U.S. application No. 08/878,188, Gordon, et al., filed Jun. 18, 1998

*Primary Examiner*—Mark Kopec
*Assistant Examiner*—Gregory R. Delcotto
*Attorney, Agent, or Firm*—Darryl C. Little

[57] ABSTRACT

A liquid personal cleansing composition comprising: (a) from about 1% to about 15% by weight of short chain alkyl sulphate surfactant having an average of from 8 to 10 carbon atoms in the alkyl chain and mixtures thereof; (b) from about 1% to about 60% by weight of water-soluble auxiliary surfactant selected from anionic surfactant other than $C_8$ to $C_{10}$ alkyl sulphate, nonionic, zwitterionic and amphoteric surfactants and mixtures thereof; (c) from about 0.01% to about 5% by weight of cationic polymeric skin conditioning agent; and (d) water. The products demonstrate excellent in-use efficacy benefits including mildness, a moisturised skin feel, excellent rinsibility and good product stability and lather attributes.

18 Claims, No Drawings

LIQUID PERSONAL CLEANSING COMPOSITION CONTAINING CATIONIC POLYMERIC SKIN CONDITIONING AGENT

The present invention relates to cleansing compositions. In particular it relates to mild personal cleansing compositions with good skin feel attributes, rinsing behaviour and foaming properties which are suitable for simultaneously cleansing and conditioning the skin and/or the hair and which may be used, for example, in the form of foam bath preparations, shower products, skin cleansers, hand, face and body cleansers, shampoos, etc.

BACKGROUND OF THE INVENTION

Mild cosmetic compositions must satisfy a number of criteria including cleansing power, foaming properties and mildness/low irritancy/good feel with respect to the skin, hair and the ocular mucosae. Skin is made up of several layers of cells which coat and protect the keratin and collagen fibrous proteins that form the skeleton of its structure. The outermost of these layers, referred to as the stratum corneum, is known to be composed of 250 Å protein bundles surrounded by 80 Å thick layers. Hair similarly has a protective outer coating enclosing the hair fibre which is called the cuticle. Anionic surfactants can penetrate the stratum corneum membrane and the cuticle and, by delipidization destroy membrane integrity. This interference with skin and hair protective membranes can lead to a rough skin feel and eye irritation and may eventually permit the surfactant to interact with the keratin and hair proteins creating irritation and loss of barrier and water retention functions.

Ideal cosmetic cleansers should cleanse the skin or hair gently, without defatting and/or drying the hair and skin and without irritating the ocular mucosae or leaving skin taut after frequent use. Most lathering soaps, shower and bath products, shampoos and bars fail in this respect.

Certain synthetic surfactants are known to be mild. However, a major drawback of most mild synthetic surfactant systems when formulated for shampooing or personal cleansing is poor lather performance compared to the highest shampoo and bar soap standards. Thus, surfactants that are among the mildest are marginal in lather. The use of known high sudsing anionic surfactants such as alkyl sulphates with lather boosters, on the other hand, can yield acceptable lather volume and quality but at the expense of clinical skin mildness. These two facts make the surfactant selection, the lather and mildness benefit formulation process a delicate balancing act.

Thus a need exists for personal cleansing products which deliver acceptable in-use skin feel characteristics but which will not dehydrate the skin or result in loss of skin suppleness, which will provide a level of skin conditioning performance in a wash and rinse-off product which previously has only been provided by a separate post-cleansing cosmetic moisturizer, which demonstrate desirable rinsing behaviour and which will produce a foam which is stable and of high quality, which are effective hair and skin cleansers, which have good rinsibility characteristics, and which at the same time have stable product and viscosity characteristics and remain fully stable under long term and stressed temperature storage conditions.

It has now been found that personal cleansing compositions having improved skin feel and moisturisation attributes, both in use and after use, which deliver desirable rinsing benefits and good product stability can be formed by the combination of short chain alkyl sulphates with cationic polymers and mild surfactants and/or nonionic surfactants. Surprisingly, the combination of short chain (high CMC) alkyl sulphate and cationic polymer is particularly advantageous for skin mildness benefits and at the same time provides good lathering characteristics especially in applications which involve concentrated usage or direct application to skin such as shower products, hand and skin cleansers and the like. It has also been found that combinations of short chain alkyl sulphates with particular alkyl ethoxysulphate surfactants confer particular benefits in personal cleansing compositions in terms of mildness and rinsing characteristics.

SUMMARY OF THE INVENTION

The subject of the present invention is a mild, foam-producing, easily rinsed, stable cleansing product suitable for personal cleansing of the skin or hair and which may be used as shower products, skin cleansers and shampoos etc. According to one aspect of the invention, there is provided a liquid personal cleansing composition comprising:

(a) from about 1% to about 15% by weight of short chain alkyl sulphate surfactant having an average of from 8 to 10 carbon atoms on the alkyl chain and mixtures thereof;

(b) from about 1% to about 60% by weight of water-soluble auxiliary surfactant selected from anionic surfactant other than $C_8$ to $C_{10}$ alkyl sulphate, nonionic, zwitterionic and amphoteric surfactants and mixtures thereof;

(c) from about 0.01% to about 5% by weight of cationic polymeric skin conditioning agent; and (d) water According to another aspect of the invention there is provided a personal cleansing composition comprising:

(a) from about 1% to about 15% by weight of short chain alkyl sulphate surfactant having on average from 8 to 10 carbon atoms on the alkyl chain and mixtures thereof;

(b) from about 1% to about 15% by weight of $C_{12}$ to $C_{22}$ alkyl ethoxy sulphate surfactant having an average degree of ethoxylation of from about 1 to about 6;

(c) from about 0.1% to about 10% of water-soluble auxiliary surfactant selected from anionic surfactant other than $C_8$ to $C_{10}$ alkyl sulphate, nonionic, zwitterionic and amphoteric and mixtures thereof; and optionally (d) from about 0.01% to about 5% of cationic conditioning polymer; and (e) water.

wherein the ratio of short chain alkyl sulphate to alkyl ethoxy sulphate is in the range of from about 1:3 to about 3:1, more preferably from about 2:1 to about 1:2.

According to a further embodiment of the invention there is provided a personal cleansing composition comprising:

(a) from about 1% to about 15% by weight of short chain alkyl sulphate surfactant having on average from 8 to 10 carbon atoms on the alkyl chain and mixtures thereof;

(b) from about 0.1% to about 20% by weight of a nonionic polyhydroxy fatty acid amide surfactant having the general formula (II).

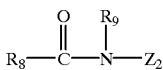

wherein $R_8$ is $C_5$–$C_{31}$ hydrocarbyl, $R_9$ is $C_1$–$C_8$ alkyl or hydroxyalkyl and $Z_2$ is a polyhydroxyhydrocarbyl moiety.

(c) from about 1% to about 60% by weight of water-soluble auxiliary surfactant selected from anionic surfactant other than $C_8$ to $C_{10}$ alkyl sulphate, other nonionic, zwitterionic and amphoteric surfactants and mixtures thereof;

(d) water.

In a highly preferred embodiment, the invention takes the form of a foam producing liquid cleansing composition with superior skin feel and mildness characteristics, excellent rinsing behaviour, improved perceived dryness and expertly graded dryness and skin hydration measurements and trans epidermal water loss (TEWL), combined with excellent lathering, good stability, cleansing ability and conditioning performance.

All concentrations and ratios herein are by weight of the cleansing composition, unless otherwise specified. Surfactant chain lengths are also on a weight average chain length basis, unless otherwise specified.

The liquid cleansing compositions herein are based on a combination of short chain alkyl sulphates with other mild surfactants and polymeric skin conditioning agents. Preferred embodiments also contain perfume or cosmetic oils.

The compositions of the present invention contain, as an essential component, a short chain alkyl sulphate surfactant where 'short chain' as defined herein means an average carbon chain length of $C_{10}$ or less. The short chain alkyl sulphate surfactants of the present invention are valuable in shower gel compositions for the delivery of improved skin mildness attributes and product rinsing benefits in combination with a desirable lather profile. Alkyl sulphate surfactants suitable for inclusion in the compositions of the present invention have the general formula (I);

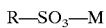

wherein R is straight or branched chain alkyl, preferably straight chain, containing on average from about 8 to about 10 carbon atoms, preferably about 10 carbon atoms and wherein M is selected from alkali metals, ammonium or other suitable monovalent cation or mixtures thereof. It should be understood that the definition of any particular carbon chain length, say $C_8$ is an average value and as such may contain certain proportions of both higher and lower carbon chain lengths as a direct function of its synthesis. The level of such material can be achieved by modification of the process and the nature of the starting materials. While $C_{10}$ alkyl sulphate is the preferred surfactant in the compositions of the invention mixtures of short chain alkyl sulphates may also be used. Especially preferred in the compositions herein is $C_{10}$ alkyl sulphate material containing at least about 80% by weight of the $C_{10}$, preferably at least about 90% $C_{10}$, more preferably at least about 95% $C_{10}$ and especially at least about 99% $C_{10}$ alkyl sulphate. Suitable short chain alkyl sulphate materials are available from Albright and Wilson under the trade names Empicol LC35 and Empicol 0758F. The short chain alkyl sulphate is present in the compositions herein described at a level of from about 1% to about 10%, more preferably from about 2% to about 5% by weight.

As a further essential feature the compositions of the present invention comprise a mild surfactant system of water-soluble auxiliary surfactants. Mild surfactants suitable for inclusion in compositions according to the present invention generally have a lipophilic chain length of from about 12 to about 22 carbon atoms and can be selected from anionic, nonionic, zwitterionic and amphoteric surfactants and mixtures thereof. The total level of auxiliary surfactant is preferably from about 3% to about 40%, more preferably from about 4% to about 20%, and especially from about 5% to about 15% by weight. The compositions preferably comprise a mixture of anionic with zwitterionic and/or amphoteric surfactants. The level of the individual auxiliary anionic, zwitterionic and amphoteric surfactant components, where present, is in the range from about 1% to about 15%, and especially from about 2% to about 13% by weight of the composition, while the level of nonionic surfactant, where present, is in the range from about 0.1% to about 20% by weight, preferably from about 0.5% to about 16%, more preferably from about 1% to about 12% by weight. The weight ratio of auxiliary anionic surfactant: zwitterionic and/or amphoteric surfactant is in the range from about 1:2 to about 6:1. Other suitable compositions within the scope of the invention comprise mixtures of anionic, zwitterionic and/for amphoteric surfactants with one or more nonionic surfactants. Preferred for use herein are soluble or dispersible nonionic surfactants selected from ethoxylated animal and vegetable oils and fats and mixtures thereof, sometimes referred to herein as "oil-derived" nonionic surfactants.

Auxiliary anionic surfactants suitable for inclusion in the compositions of the invention can generally be described as mild synthetic detergent surfactants and include ethoxylated alkyl sulphates, alkyl glyceryl ether sulfonates, methyl acyl taurates, fatty acyl glycinates, N-acyl glutamates, acyl isethionates, alkyl sulfosuccinates, alkyl ethoxysulphosuccinates, alpha-sulfonated fatty acids, their salts and/or their esters, alkyl ethoxy carboxylates, alkyl phosphate esters, ethoxylated alkyl phosphate esters, alkyl sulphates, acyl sarcosinates and fatty acid/protein condensates, and mixtures thereof. Alkyl and/or acyl chain lengths for these surfactants are $C_{12}$–$C_{22}$, preferably $C_{12}$–$C_{18}$ more preferably $C_{12}$–$C_{14}$.

Preferred for use herein from the viewpoint of optimum mildness and lathering characteristics are the salts of sulfuric acid esters of the reaction product of 1 mole of a higher fatty alcohol and from about 1 to about 12 moles of ethylene oxide, with sodium and magnesium being the preferred counterions. Particularly preferred are the alkyl sulfates containing from about 1 to 6, preferably 2 to 4 moles of ethylene oxide, such as sodium laureth-2 sulfate, sodium laureth-3 sulfate and magnesium sodium laureth-3.6 sulfate and especially preferred is sodium laureth-3 sulphate. In preferred embodiments, the anionic surfactant contains at least about 50%, especially at least about 75% by weight of ethoxylated alkyl sulfate.

In addition to the broad range ethoxylated alkyl sulphates obtained via conventional sodium catalysed ethoxylation techniques and subsequent sulphation processes, ethoxylated alkyl sulphates obtained from narrow range ethoxylates (NREs) are particularly suitable for use in the present compositions. Narrow range ethoxylated alkyl sulphates are particularly valuable in the compositions of the invention for the delivery of improved skin mildness and product lather attributes. Narrow range ethoxylated alkyl sulphates suitable for use herein are selected from sulphated alkyl ethoxylates containing on average from about 1 to about 6, preferably from about 2 to about 4 and especially about 3 moles of ethylene oxide such as NRE sodium laureth-3 sulphate. NRE materials suitable for use herein contain distributions of the desired ethylene oxide ($EO_n$) in the ranges of from 15% to about 30% by weight of $EO_n$, from about 10% to about 20% by weight of $EO_{n+1}$ and from about 10% to about 20% by weight of $EO_{n-1}$. Highly preferred NRE materials contain less than about 5% by weight of ethoxylated alkyl sulphate having 6 or more moles of ethylene oxide and less than about 5% by weight of non-ethoxylated alkyl sulphate.

The compositions of the invention can also comprise an auxiliary water-soluble nonionic surfactant at levels from about 0.1% to about 20%, more preferably from about 0.1% to about 10%, and especially from about 1% to about 8% by weight. Surfactants of this class include C12–C14 fatty acid mono-and diethanolamides, sucrose polyester surfactants and polyhydroxy fatty acid amide surfactants having the general formula (II).

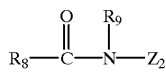

The preferred N-alkyl, N-alkoxy or N-aryloxy, polyhydroxy fatty acid amide surfactants according to formula (IX) are those in which $R_8$ is $C_5$–$C_{31}$ hydrocarbyl, preferably $C_6$–$C_{19}$ hydrocarbyl, including straight-chain and branched chain alkyl and alkenyl, or mixtures thereof and $R_9$ is typically $C_1$–$C_8$ alkyl or hydroxyalkyl, preferably methyl, or a group of formula —$R^1$—O—$R^2$ wherein $R^1$ is $C_2$–$C_8$ hydrocarbyl including straight-chain, branched-chain and cyclic (including aryl), and is preferably $C_2$–$C_4$ alkylene, $R^2$ is $C_1$–$C_8$ straight-chain, branched-chain and cyclic hydrocarbyl including aryl and oxyhydrocarbyl, and is preferably $C_1$–$C_4$ alkyl, especially methyl, or phenyl. $Z_2$ is a polyhydroxyhydrocarbyl moiety having a linear hydrocarbyl chain with at least 2 (in the case of glyceraldehyde) or at least 3 hydroxyls (in the case of other reducing sugars) directly connected to the chain, or an alkoxylated derivative (preferably ethoxylated or propoxylated) thereof. $Z_2$ preferably will be derived from a reducing sugar in a reductive amination reaction, most preferably $Z_2$ is a glycityl moiety. Suitable reducing sugars include glucose, fructose, maltose, lactose, galactose, mannose, and xylose, as well as glyceraldehyde. As raw materials, high dextrose corn syrup, high fructose corn syrup, and high maltose corn syrup can be utilized as well as the individual sugars listed above. These corn syrups may yield a mix of sugar components for $Z_2$. It should be understood that it is by no means intended to exclude other suitable raw materials. $Z_2$ preferably will be selected from the group consisting of —$CH_2$—$(CHOH)_n$—$CH_2OH$, —$CH(CH_2OH)$—$(CHOH)_{n-1}$—$CH_2H$, $CH_2(CHOH)_2(CHOR')CHOH)$—$CH_2OH$, where n is an integer from 1 to 5, inclusive, and R' is H or a cyclic mono- or poly-saccharide, and alkoxylated derivatives thereof. As noted, most preferred are glycityls wherein n is 4, particularly —$CH_2$—$(CHOH)_4$—$CH_2OH$.

The most preferred polyhydroxy fatty acid amide has the formula $R_8(CO)N(CH_3)CH_2(CHOH)_4CH_2OH$ wherein $R_8$ is a C6–C19 straight chain alkyl or alkenyl group. In compounds of the above formula, $R_8$—CO—N< can be, for example, cocoamide, stearamide, oleamide, lauramide, myristamide, capricamide, palmiamide, tallowamide, etc.

A preferred process for making the above compounds having formula (II) comprises reacting a fatty acid triglyceride with an N-substituted polyhydroxy amine in the substantial absence of lower ($C_1$–$C_4$) alcoholic solvent, but preferably with an alkoxylated alcohol or alkoxylated alkyl phenol such as NEODOL and using an alkoxide catalyst at temperatures of from about 50° C. to about 140° C. to provide high yields (90–98%) of the desired products. Suitable processes for making the desired polyhydroxy fatty acid amide compounds are outlined in U.S. Pat. No. 5,194,639 and U.S. Pat. No. 5,380,891.

The compositions for use herein suitably also contain a water-soluble auxiliary amphoteric surfactant. Amphoteric surfactants suitable for use in the compositions of the invention include:

(a) imidazolinium surfactants of formula (III)

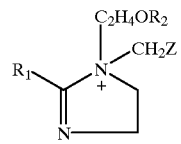

wherein $R_1$ is $C_7$–$C_{22}$ alkyl or alkenyl, $R_2$ is hydrogen or $CH_2Z$, each Z is independently $CO_2M$ or $CH_2CO_2M$, and M is H, alkali metal, alkaline earth metal, ammonium or alkanolammonium; and/or ammonium derivatives of formula (IV)

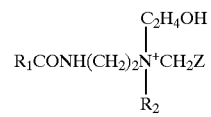

wherein $R_1$, $R_2$ and Z are as defined above;
(b) aminoalkanoates of formula (V)

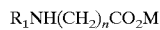

iminodialkanoates of formula (VI)

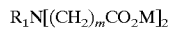

and iminopolyalkanoates of formula (VII)

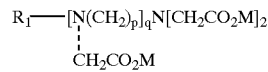

wherein n, m, p, and q are numbers from 1 to 4, and $R_1$ and M are independently selected from the groups specified above; and (c) mixtures thereof.

Suitable amphoteric surfactants of type (a) are marketed under the trade name Miranol and Empigen and are understood to comprise a complex mixture of species. Traditionally, the Miranols have been described as having the general formula III, although the CTFA Cosmetic Ingredient Dictionary, 3rd Edition indicates the non-cyclic structure IV while the 4th Edition indicates yet another structural isomer in which $R_2$ is O-linked rather than N-linked. In practice, a complex mixture of cyclic and non-cyclic species is likely to exist and both definitions are given here for sake of completeness. Preferred for use herein, however, are the non-cyclic species.

Examples of suitable amphoteric surfactants of type (a) include compounds of formula III and/or IV in which $R_1$ is $C_8H_{17}$ (especially iso-capryl), $C_9H_{19}$ and $C_{11}H_{23}$ alkyl. Especially preferred are the compounds in which $R_1$ is $C_9H_{19}$, Z is $CO_2M$ and $R_2$ is H; the compounds in which $R_1$ is $C_{11}H_{23}$, Z is $CO_2M$ and $R_2$ is $CH_2CO_2M$; and the compounds in which $R_1$ is $C_{11}H_{23}$, Z is $CO_2M$ and $R_2$ is H.

In CTFA nomenclature, materials suitable for use in the present invention include cocoamphocarboxypropionate, cocoamphocarboxy propionic acid, and especially cocoamphoacetate and cocoamphodiacetate (otherwise referred to as cocoamphocarboxyglycinate). Specific commercial products include those sold under the trade names of Ampholak 7TX (sodium carboxy methyl tallow polypropyl amine), Empigen CDL60 and CDR 60 (Albright & Wilson), Miranol H2M Conc. Miranol C2M Conc. N.P., Miranol C2M Conc. O.P., Miranol C2M SF, Miranol CM Special (Rhône-Poulenc); Alkateric 2CIB (Alkaril Chemicals); Amphoterge W-2 (Lonza, Inc.); Monateric CDX-38, Monateric CSH-32 (Mona Industries); Rewoteric AM-2C (Rewo Chemical Group); and Schercotic MS-2 (Scher Chemicals).

It will be understood that a number of commercially-available amphoteric surfactants of this type are manufactured and sold in the form of electroneutral complexes with, for example, hydroxide counterions or with anionic sulfate or sulfonate surfactants, especially those of the sulfated $C_8$–$C_{18}$ alcohol, $C_8$–$C_{18}$ ethoxylated alcohol or $C_8$–$C_{18}$ acyl glyceride types. Preferred from the viewpoint of mildness and product stability, however, are compositions which are essentially free of (non-ethoxylated) sulfated alcohol surfactants. Note also that the concentrations and weight ratios of the amphoteric surfactants are based herein on the uncomplexed forms of the surfactants, any anionic surfactant counterions being considered as part of the overall anionic surfactant component content.

Examples of preferred amphoteric surfactants of type (b) include N-alkyl polytrimethylene poly-, carboxymethylamines sold under the trade names Ampholak X07 and Ampholak 7CX by Berol Nobel and also salts, especially the triethanolammonium salts and salts of N-lauryl-beta-amino propionic acid and N-lauryl-imino-dipropionic acid. Such materials are sold under the trade name Deriphat by Henkel and Mirataine by Rhône-Poulenc.

The compositions herein can also contain from about 0.1% to about 20%, more preferably from about 0.1% to about 10%, and especially from about 1% to about 8% of a zwitterionic surfactant.

Water-soluble auxiliary betaine surfactants suitable for inclusion in the compositions of the present invention include alkyl betaines of the formula $R_5R_6R_7N^+$ $(CH_2)_nCO_2M$ (VIII) and amido betaines of the formula (IX)

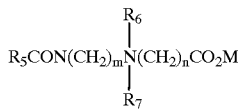

wherein $R_5$ is $C_{11}$–$C_{22}$ alkyl or alkenyl, $R_6$ and $R_7$ are independently $C_1$–$C_3$ alkyl, M is H, alkali metal, alkaline earth metal, ammonium or alkanolammonium, and n, m are each numbers from 1 to 4. Preferred betaines include cocoamidopropyldimethylcarboxymethyl betaine, laurylamidopropyldimethylcarboxymethyl betaine and Tego betaine (RTM).

Water-soluble auxiliary sultaine surfactants suitable for inclusion in the compositions of the present invention include alkyl sultaines of the formula (X);

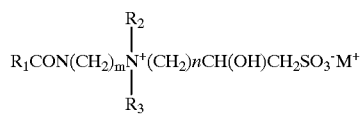

wherein $R_1$ is $C_7$ to $C_{22}$ alkyl or alkenyl, $R_2$ and $R_3$ are independently $C_1$ to $C_3$ alkyl, M is H, alkali metal, alkaline earth metal, ammonium or alkanolammonium and m and n are numbers from 1 to 4. Preferred for use herein is coco amido propylhydroxy sultaine.

Water-soluble auxiliary amine oxide surfactants suitable for inclusion in the compositions of the present invention include alkyl amine oxide $R_5R_6R_7NO$ and amido amine oxides of the formula (XI)

wherein $R_5$ is $C_{11}$ to $C_{22}$ alkyl or alkenyl, $R_6$ and $R_7$ are independently $C_1$ to $C_3$ alkyl, M is H, alkali metal, alkaline earth metal, ammonium or alkanolammonium and m is a number from 1 to 4. Preferred amine oxides include cocoamidopropylamine oxide, lauryl dimethyl amine oxide and myristyl dimethyl amine oxide.

The compositions according to the present invention can also a skin conditioning cationic polymer. The cationic polymer is valuable in the compositions according to the present invention for provision of skin feel attributes and for improved rheology and application characteristics in the presence of the hydrophobically modified cellulose ether moiety. The polymeric skin conditioning agent is preferably present at a level from about 0.01% to about 5%, preferably from about 0.01% to about 3% and especially from about 0.01% to about 2% by weight.

Suitable polymers are high molecular weight materials (mass-average molecular weight determined, for instance, by light scattering, being generally from about 2,000 to about 5,000,000, preferably from about 5,000 to about 3,000,000 more preferably from 100,000 to about 1,000,000).

Representative classes of polymers include cationic polysaccharides; cationic homopolymers and copolymers derived from acrylic and/or methacrylic acid; cationic cellulose resins; cationic copolymers of dimethyldiallylammonium chloride and acrylamide and or acrylic acid; cationic homopolymers of dimethyldiallylammonium chloride; cationic polyalkylene and ethoxypolyalkylene imines; quaternized silicones, and mixtures thereof.

By way of exemplification, cationic polymers suitable for use herein include cationic guar gums such as hydroxypropyl trimethyl ammonium guar gum (d.s. of from 0.11 to 0.22) available commercially under the trade names Jaguar C-14-S(RTM) and Jaguar C-17(RTM) and also Jaguar C-16 (RTM), which contains hydroxypropyl substituents (d.s. of from 0.8–1.1) in addition to the above-specified cationic groups, and quaternized hydroxy ethyl cellulose ethers available commercially under the trade names Ucare Polymer JR-30M, JR400, Catanal (RTM) and Celquat. Other suitable cationic polymers are homopolymers of dimethyldiallylammonium chloride available commercially under the trade name Merquat 100, copolymers of dimethyl aminoethylmethacrylate and acrylamide, copolymers of dimethyldiallylammonium chloride and acrylamide, available commercially under the trade names Merquat 550 and Merquat S, acrylic acid/dimethyldiallylammonium chloride/ acrylamide copolymers available under the trade name Merquat 3300, quaternized vinyl pyrrolidone acrylate or methacrylate copolymers of amino alcohol available commercially under the trade name Gafquat, for example Polyquaternium 11, 23 and 28 (quaternized copolymers of vinyl pyrrolidone and dimethyl aminoethylmethacrylate—Gafquat 755N and HS-1 00), vinyl pyrrolidone/vinyl imidazolium methochloride copolymers available under the trade names Luviquat HM552, Polyquaternium 2, and polyalkyleneimines such as polyethylenimine and ethoxylated polyethylenimine.

The compositions of the invention preferably also contain from about 0.1% to about 20%, preferably from about 1% to about 15%, and more preferably from about 2% to about 10% by weight of an oil derived nonionic surfactant or mixture of oil derived nonionic surfactants. Oil derived nonionic surfactants are valuable in compositions according to the invention for the provision of skin feel benefits both in use and after use. Suitable oil derived nonionic surfactants for use herein include water soluble vegetable and animal-derived emollients such as triglycerides with a polyethyleneglycol chain inserted; ethoxylated mono and di-glycerides, polyethoxylated lanolins and ethoxylated butter derivatives. One preferred class of oil-derived nonionic surfactants for use herein have the general formula (XII)

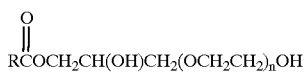

wherein n is from about 5 to about 200, preferably from about 20 to about 100, more preferably from about 30 to about 85, and wherein R comprises an aliphatic radical having on average from about 5 to 20 carbon atoms, preferably from about 7 to 18 carbon atoms.

Suitable ethoxylated oils and fats of this class include polyethyleneglycol derivatives of glyceryl cocoate, glyceryl caproate, glyceryl caprylate, glyceryl tallowate, glyceryl palmate, glyceryl stearate, glyceryl laurate, glyceryl oleate, glyceryl ricinoleate, and glyceryl fatty esters derived from triglycerides, such as palm oil, almond oil, and corn oil, preferably glyceryl tallowate and glyceryl cocoate.

Suitable oil derived nonionic surfactants of this class are available from Croda Inc. (New York, USA) under their Crovol line of materials such as Crovol EP40 (PEG 20 evening primrose glyceride), Crovol EP 70 (PEG 60 evening primrose glyceride) Crovol A40 (PEG 20 almond glyceride), Crovol A-70 (PEG 60 almond glyceride), Crovol M40 (PEG 20 maize glyceride), Crovol M-70 (PEG 60 maize glyceride), Crovol PK40 (PEG 12 palm kernel glyceride), and Crovol PK-70 (PEG 45 palm kernel glyceride) and under their Solan range of materials such as Solan E, E50 and X polyethoxylated lanolins and Aqualose L-20 (PEG 24 lanolin alcohol) and Aqualose W15 (PEG 15 lanolin alcohol) available from Westbrook Lanolin. Further suitable surfactants of this class are commercially available from Sherex Chemical Co. (Dublin, Ohio, USA) under their Varonic LI line of surfactants and from Rewo under their Rewoderm line of surfactants. These include, for example, Varonic LI 48 (polyethylene glycol (n=80) glyceryl tallowate, alternatively referred to as PEG 80 glyceryl tallowate), Varonic LI 2 (PEG 28 glyceryl tallowate), Varonic LI 420 (PEG 200 glyceryl tallowate), and Varonic LI 63 and 67 (PEG 30 and PEG 80 glyceryl cocoates), Rewoderm L15–20 (PEG-200 palmitate), Rewoderm LIS80 (PEG-200 palmitate with PEG-7 glyceryl cocoate) and Rewoderm LIS-75 (PEG-200 palmitate with PEG-7 glyceryl cocoate) and mixtures thereof. Other oil-derived emollients suitable for use are PEG derivatives of corn, avocado, and babassu oil, as well as Softigen 767 (PEG(6) caprylic/capric glycerides).

Also suitable for use herein are nonionic surfactants derived from composite vegetable fats extracted from the fruit of the Shea Tree (Butyrospermum Karkii Kotschy) and derivatives thereof. This vegetable fat, known as Shea Butter is widely used in Central Africa for a variety of means such as soap making and as a barrier cream, it is marketed by Sederma (78610 Le Perray En Yvelines, France). Particularly suitable are ethoxylated derivatives of Shea butter available from Karlshamn Chemical Co. (Columbos, Ohio, USA) under their Lipex range of chemicals, such as Lipex 102 E-75 and Lipex 102 E-3 (ethoxylated mono, di-glycerides of Shea butter) and from Croda Inc. (New York, USA) under their Crovol line of materials such as Crovol SB-70 (ethoxylated mono, di-glycerides of Shea butter). Similarly, ethoxylated derivatives of Mango, Cocoa and Illipe butter may be used in compositions according to the invention. Although these are classified as ethoxylated nonionic surfactants it is understood that a certain proportion may remain as non-ethoxylated vegetable oil or fat.

Other suitable oil-derived nonionic surfactants include ethoxylated derivatives of almond oil, peanut oil, rice bran oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grapeseed oil, and sunflower seed oil.

Oil derived nonionic surfactants highly preferred for use herein from the viewpoint of optimum mildness and skin feel characteristics are Lipex 102-3 (RTM) (PEG-3 ethoxylated derivatives of Shea Butter) and Softigen 767 (RTM) (PEG6 caprylic/capric glycerides).

The compositions according to the present invention can also comprise lipophilic emulsifiers as skin care actives. Suitable lipophilic skin care actives include anionic food grade emulsifiers which comprise a di-acid mixed with a monoglyceride such as succinylated monoglycerides, monostearyl citrate, glyceryl monostearate diacetyl tartrate and mixtures thereof.

The compositions of the invention may also include an insoluble perfume or cosmetic oil or wax or a mixture thereof at a level up to about 10%, preferably up to about 3% by weight wherein the oil or wax is insoluble in the sense of being insoluble in the product matrix at a temperature of 25° C. Addition of such oils or waxes can provide emolliency, mildness and rinsibility characteristics to personal cleansing compositions according to the invention. It is a feature of the invention, however, that compositions having excellent emolliency and mildness together with desirable physical attributes (clarity etc.) can be delivered which are essentially oil-free, ie which contain less than about 1%, preferably less than 0.5% by weight of an added oil phase. Physically, preferred compositions of this type take the form of an optically-clear solution or microemulsion. In compositions including an additional perfume or cosmetic oil or wax, preferably the weight ratio of oil-derived nonionic surfactant to added oil is at least about 1:2, more especially at least about 3:1.

Suitable insoluble cosmetic oils and waxes for use herein can be selected from water-insoluble silicones inclusive of non-volatile polyalkyl and polyaryl siloxane gums and fluids, volatile cyclic and linear polyalkylsiloxanes, polyalkoxylated silicones, amino and quaternary ammonium modified silicones, rigid cross-linked and reinforced silicones and mixtures thereof, $C_1$–$C_{24}$ esters of $C_8$–$C_{30}$ fatty acids such as isopropyl myristate, myristyl myristate and cetyl ricinoleate, $C_8$–$C_{30}$ esters of benzoic acid, beeswax, saturated and unsaturated fatty alcohols such as behenyl alcohol, hydrocarbons such as mineral oils, petrolatum squalane and squalene, polybutene, fatty sorbitan esters (see U.S. Pat. No. 3,988,255, Seiden, issued October 26th 1976), lanolin and oil-like lanolin derivatives, animal and vegetable triglycerides such as almond oil, peanut oil, wheat germ oil, rice bran oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soyabean oil, avocado oil, safflower oil, coconut oil, hazelnut oil, olive oil, grapeseed oil, and sunflower seed oil, and $C_1$–$C_{24}$ esters of dimer and trimer acids such as diisopropyl dimerate, diisostearylmalate, diisostearyldimerate and triisostearyltrimerate.

Nonionic water-soluble cellulose ethers can be used as additional skin moisturising agents in the compositions according to the present inventions Widely used, commercially-available nonionic cellulose ethers include methyl cellulose, hydroxy propyl methyl cellulose, hydroxyethylcellulose, hydroxypropyl cellulose and ethyl hydroxyethyl cellulose. Particularly preferred for use as moisturisation aids are hydrophobically modified hydroxy ethyl cellulose materials. One commercially available material suitable for use herein is NATROSOL PLUS Grade 330 CS (RTM), a hydrophobically modified hydroxyethylcellulose available from Aqualon Company, Wilmington, Del. This material has a $C_{16}$ alkyl substitution of from 0.4% to 0.8% by weight. The hydroxyethyl molar substitution for this material is from 3.0 to 3.7. The average molecular weight for the water-soluble cellulose prior to modification is approximately 300,000. Another material of this type is sold under the trade name NATROSOL PLUS CS Grade D-67 (RTM), by Aqualon Company, Wilmington, Del. This material has a $C_{16}$ substitution of from 0.50% to 0.95%, by weight. The hydroxyethyl molar substitution for this material is from 2.3 to 3.7. The average molecular weight for the water soluble cellulose prior to modification is approximately 700,000.

The present compositions can also comprise a nonionic or anionic polymeric thickening component, especially a water-soluble polymeric materials, having a molecular weight greater than about 20,000. By "water-soluble polymer" is meant that the material will form a substantially clear solution in water at a 1% concentration at 25° C. and the material will increase the viscosity of the water. Examples of water-soluble polymers which may desirably be used as an additional thickening component in the present compositions, are hydroxyethylcellulose, hydroxypropyl cellulose, hydroxypropyl methylcellulose, polyethylene glycol, polyacrylamide, polyacrylic acid, polyvinyl alcohol, polyvinyl pyrrolidone K-120, dextrans, for example Dextran purified crude Grade 2P, available from D&O Chemicals, carboxymethyl cellulose, plant exudates such as acacia, ghatti, and tragacanth, seaweed extracts such as sodium alginate, propylene glycol alginate and sodium carrageenan. Preferred as the additional thickeners for the present compositions are natural polysaccharide materials. Examples of such materials are guar gum, locust bean gum, and xanthan gum. Also suitable herein preferred is hydroxyethyl cellulose having a molecular weight of about 700,000.

Additional polymeric thickening agents include acrylic acid/ethyl acrylate copolymers and the carboxyvinyl polymers sold by the B.F. Goodrich Company under the trade mark of Carbopol resins. These resins consist essentially of a colloidally water-soluble polyalkenyl polyether crosslinked polymer of acrylic acid crosslinked with from 0.75% to 2.00% of a crosslinking agent such as for example polyallyl sucrose or polyallyl pentaerythritol. Examples include Carbopol 934, Carbopol 940, Carbopol 950, Carbopol 980, Carbopol 951 and Carbopol 981. Carbopol 934 is a water-soluble polymer of acrylic acid crosslinked with about 1% of a polyallyl ether of sucrose having an average of about 5.8 alkyl groups for each sucrose molecule. Also suitable for use herein are hydrophobically-modified crosslinked polymers of acrylic acid having amphipathic properties available under the Trade Name Carbopol 1382, Carbopol 1342 and Pemulen TR-1 (CFTA Designation: Acrylates/10–30 Alkyl Acrylate Crosspolymer). A combination of the polyalkenyl polyether cross-linked acrylic acid polymer and hydrophobically modified cross-linked acrylic acid polymer is also suitable for use herein.

The polymeric thickening component, if present in the compositions of the present invention, is at a level of from 0.3% to 5.0%, preferably from 0.4% to 3.0% by weight.

Further additional thickening agents suitable for use herein include ethylene glycol or polyethylene glycol esters of a fatty acid having from about 16 to about 22 carbon atoms and up to 7 ethyleneoxy units, preferably the ethylene glycol stearates, both mono and distearate, but particularly the distearate containing less than about 7% of the mono stearate, alkanolamides of fatty acids, having from about 16 to about 22 carbon atoms, preferably about 16 to 18 carbon atoms such as stearic monoethanolamide, stearic diethanolamide, stearic monoisopropanolamide and stearic monoethanolamide, alkyl ($C_{16}$–$C_{22}$) dimethyl amine oxides such as stearyl dimethyl amine oxide and electrolytes such as magnesium sulphate and sodium chloride salts. Fatty alcohol or fatty acid materials having from about 12 to about 22 carbon atoms as thickening components are also suitable for use as thickening agents in the compositions of the present invention. Suitable fatty acid and fatty alcohol thickeners include Laurex NC (C12/14 fatty alcohol) available from Albright and Wilson and Prifac 7908 (palm kernel fatty acid) available from Unichema.

The viscosity of the final composition (Brookfield RVT DCP, 1 rpm with Cone CP41 or CP52, 25° C., neat) is preferably at least about 500 cps, more preferably from about 1,000 to about 50,000 cps, especially from about 4,000 to about 30,000 cps, more especially from about 4,000 to about 15,000 cps.

The cleansing compositions can optionally include other hair or skin moisturizers which are soluble in the cleansing composition matrix. The preferred level of such moisturizers is from about 0.5% to about 20% by weight. In preferred embodiments, the moisturizer is selected from essential amino acid compounds found naturally occurring in the stratum corneum of the skin and water-soluble nonpolyol nonocclusives and mixtures thereof.

Some examples of more preferred nonocclusive moisturizers are polybutene, squalane, sodium pyrrolidone carboxylic acid, lactic acid, L-proline, guanidine, pyrrolidone, hydrolyzed protein and other collagen-derived proteins, alas vera gel, acetamide MEA and lactamide MEA and mixtures thereof.

Compositions according to the present invention may also include an opacifier or pearlescing agent. Such materials may be included at a level of from about 0.01% to about 5%, preferably from about 0.2% to about 1.3% by weight. A suitable opacifier for inclusion in the present compositions is a polystyrene dispersion available under the trade names Lytron 621 & 631 (RTM) from Morton International.

Additional opacifiers/pearlescers suitable for inclusion in the compositions of the present invention include: titanium dioxide, $TiO_2$; EUPERLAN 810 (RTM); TEGO-PEARL (RTM); long chain ($C_{16}$–$C_{22}$) acyl derivatives such as glycol or polyethylene glycol esters of fatty acid having from about 16 to about 22 carbon atoms and up to 7 ethyleneoxy units; alkanolamides of fatty acids, having from about 16 to about 22 carbon atoms, preferably about 16 to 18 carbon atoms such as stearic monoethanolamide, stearic diethanolamide, stearic monoisopropanolamide and stearic monoethanolamide and alkyl ($C_{16}$–$C_{22}$) dimethyl amine oxides such as stearyl dimethyl amine oxide.

In preferred compositions the opacifier/pearlescer is present in the form of crystals. In highly preferred compositions the opacifier/pearlescer is a particulate polystyrene dispersion having a particle size of from about 0.05 microns to about 0.45 microns, preferably from about 0.17 microns to about 0.3 microns, such dispersions being preferred from the viewpoint of providing optimum rheology and shear-thinning behaviour. Highly preferred is styrene PVP copolymer and Lyton 631 (RTM).

A number of additional optional materials can be added to the cleansing compositions each at a level of from about 0.1% to about 2% by weight. Such materials include proteins and polypeptides and derivatives thereof; water-soluble or solubilizable preservatives such as DMDM Hydantoin, Germall 115, methyl, ethyl, propyl and butyl esters of hydroxybenzoic acid, EDTA, Euxyl (RTM) K400, natural preservatives such as benzyl alcohol, potassium sorbate and bisabalol; sodium benzoate and 2-phenoxyethanol; other moisturizing agents such as hyaluronic acid, chitin, and starch-grafted sodium polyacrylates such as Sanwet (RTM) IM-1000, IM-1500 and IM-2500 available from Celanese Superabsorbent Materials, Portsmith, Va., USA and described in U.S. Pat. No. 4,076,663; solvents; anti-bacterial agents such as Oxeco (phenoxy isopropanol); low temperature phase modifiers such as ammonium ion sources (e.g. $NH_4$ Cl); viscosity control agents such as magnesium sulfate and other electrolytes; colouring agents; $TiO_2$ and $TiO_2$-coated mica; perfumes and perfume solubilizers; and zeolites such as Valfour BV400 and derivatives thereof and $Ca^{2+}/Mg^{2+}$ sequestrants such as polycarboxylates, amino polycarboxylates, polyphosphonates, amino polyphosphonates, EDTA etc and water softening agents such as sodium citrate. Water is also present at a level preferably of from about 15% to about 97.99%, preferably from about 40% to about 90%, more preferably at least about 65% by weight of the compositions herein.

The pH of the compositions is preferably from about 4 to about 10, more preferably from about 6 to about 9, especially from about 5 to about 7.

The invention is illustrated by the following non-limiting examples.

In the examples, all concentrations are on a 100% active basis and the abbreviations have the following designation:

Amphoteric 1  Cocoamphodiacetate
Amphoteric 2  Cocoamidopropyl hydroxy sultaine
Anionic 1  Sodium C10 alkyl sulphate
Anionic 2  Sodium laureth-3 sulfate
Anionic 3  Sodium laureth sulphosuccinate
Nonionic  PEG-3 Shea butter
GA  Polyhydroxy fatty acid amide of formula IX in which $R_8$ is $C_{11}$–$C_{17}$ alkyl, $R_9$ is methyl, and $Z_2$ is $CH_2(CHOH)_4CH_2OH$
Polymer 1  Polymer JR-400(RTM) - hydroxyethylcellulose reacted with epichlorohydrin and quaternized with trimethylamine, m. wt. $4 \times 10^6$
Polymer 2  Gafquat 755N
Pearlescer  Ethyleneglycoldistearate/emulsifier mixture
Softigen 767  PEG(6) caprylic/capric glycerides
Thickener 1  C12/14 fatty alcohol
Thickener 2  PEG-200 tallowate

Examples I to XIII

The following are personal cleansing compositions in the form of shower gel or bath foam products and which are representative of the present invention:

|  | I | II | III | IV | V | VI | VII | VIII | IX | X | XI | XII |
|---|---|---|---|---|---|---|---|---|---|---|---|---|
| Anionic 1 | 4.0 | 4.0 | 2.0 | 2.0 | 3.0 | 3.0 | 3.0 | 2.0 | 2.0 | 5.0 | 1.0 | 2.0 |
| Anionic 2 | 10.0 | — | — | — | 2.0 | 5.0 | — | — | 3.0 | 2.0 | 3.0 | — |
| Anionic 3 | — | — | 5.0 | 5.0 | — | — | 3.0 | — | — | — | — | — |
| Ampho-teric 1 | — | 3.0 | 3.0 | — | 1.0 | — | — | 2.0 | — | — | 2.0 | 2.0 |
| Ampho-teric 2 | — | — | — | 3.0 | — | — | 1.0 | — | — | — | — | — |
| Betaine | 5.0 | — | — | — | — | 3.0 | 3.0 | — | 4.0 | 3.0 | — | — |
| GA | — | — | — | — | — | — | — | 5.0 | — | 3.0 | 3.0 | 5.0 |
| Nonionic | — | — | — | — | — | 1.0 | 1.0 | — | — | 1.0 | — | 1.0 |
| Polymer 1 | 0.1 | 0.1 | 0.1 | 0.1 | 0.1 | 0.1 | 0.1 | 0.1 | — | — | 0.1 | 0.1 |
| Polymer 2 | 0.1 | — | — | — | — | 0.1 | 0.1 | — | — | — | — | — |
| Softigen 767 | — | — | — | — | — | 1.0 | — | 0.1 | — | 1.0 | — | 1.0 |
| Thickener 1 | — | — | — | — | — | 0.5 | — | — | — | — | 0.5 | — |
| Thickener 2 | — | — | — | 1.0 | — | — | 0.5 | 0.5 | 0.5 | — | — | 0.5 |
| Water | to 100 |||||||||||||

Compositions I to XII are prepared by firstly dispersing the water-soluble or colloidally water-soluble polymeric rheology modifier in water at 25° C. either in a Tri-blender (RTM) or by extended stirring prior to neutralisation with NaOH or alternative base mixture and hydration. In examples II, IV and VI the mixture can be heated to about 50° C. to enhance dispersion efficiency. Next the solubilisation agent is added with further stirring. The surfactants and other skin care agents can then be added along with the remaining water-soluble, oil-insoluble ingredients. In compositions which comprise water-insoluble ingredients an oil phase B is formed from these oil-soluble ingredients which is then admixed with A at ambient temperature. The polymeric dispersion is then added to the ambient temperature mix and finally the remaining water, preservative, opacifier and perfume are added.

The compositions have a viscosity (Brookfield RVT DCP, 1 rpm with Cone CP41 or CP52, 25° C., neat) in the range of from 500 to 50,000 cps, preferably from 1,000 to 10,000 cps.

The products provide excellent in-use and efficacy benefits including mildness, skin conditioning, skin moisturising, good product stability, cleansing, lathering and excellent rinsibility.

We claim:
1. A liquid personal cleansing composition comprising:
  (a) from about 1% to about 15% by weight or short chain alkyl sulphate surfactant having on average from 8 to about 10 carbon atoms on the alkyl chain and mixtures thereof;

(b) from about 1% to about 60% or water-soluble auxiliary surfactant selected from anionic surfactants other than $C_8$ to $C_{10}$ alkyl sulphates, nonionic, zwitterionic and amphoteric surfactants and mixtures thereof;

(c) from about 0.01% to about 5% of cationic conditioning polymer selected from the group consisting of cationic polysaccharides; cationic homopolymercan copolymers derived from acrylic acid, methacrylic acid and mixtures thereof; cationic cellulose resins; cationic copolymers or dimethsldiallyalmmonium chloride, acrylamide and acrylic acid, cationic homopolymers of dimethyldiallylammonium chloride; cationic polyalkylene and ethoxypolyalkylene imines, and mixtures thereof; and (d) water.

2. A composition according to claim 1 wherein the short chain alkyl sulphate comprises at least about 80% by weight of $C_{10}$ alkyl sulphate.

3. A composition according to claim 1 wherein the short chain alkyl sulphate is present at a level of from about 1% to about 10%.

4. A composition according to claim 1 wherein the composition has a viscosity (Brookfield RVT DCP, 1 rpm with Cone CP41 or CP52, 25° C., neat) in the range from 500 to 50,000 cps.

5. A composition according to claim 1 wherein the cationic polymeric skin conditioning agent has a mass average molecular weight in the range from about 2000 about 5,000,000.

6. A composition according to claim 1 wherein the cationic conditioning polymer is present at a level of from about 0.05% to about 4% by weight.

7. A composition according to claim 1 wherein the amphoteric surfactant is selected from:

(a) imidazolinium derivatives of formula

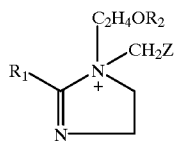

wherein $R_1$ is $C_7$–$C_{22}$ alkyl or alkenyl, $R_2$ is hydrogen of $CH_2Z$, each Z is independently $CO_2$ or $CH_2\ CO_2M$, and M is H, alkali metal, alkaline earth metal, ammonium or alkanolammonium; and/for ammonium derivatives of formula

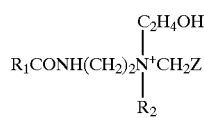

wherein $R_1$, $R_2$ and Z are as defined above:

(b) aminoalkanoates of formula

$R_1NH(CH_2)_nCO_2M$ iminodialkanoates of formula

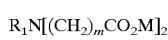

$R_1N[(CH_2)_mCO_2M]_2$ and iminopolyalkanoates of formula (VII)

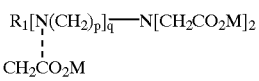

wherein n, m, p, and q are numbers from 1 to 4, and $R_1$ and M are independently selected from the groups specified above; and (c) mixtures thereof.

8. A composition according to claim 7 wherein the amphoteric is selected from imidazolinium derivatives of formula III and/or ammonium derivatives of formula IV.

9. A composition according to claim 1 wherein the water-soluble auxiliary anionic surfactant is selected from ethoxylated alkyl sulfates, alkyl glyceryl ether sulfonates, methyl acyl taurates, fatty acyl glycinates, alkyl ethoxy carboxylates, N-acyl glutamates, acyl isethionates, alkyl sulfosuccinates, alkyl ethoxy sulphosuccinates, alpha-sulfonated fatty acids, their salts and/or their esters, alkyl phosphate esters, ethoxylated alkyl phosphate esters, acyl sarcosinates and fatty acid/protein condensates, and mixtures thereof.

10. A composition according to claim 1 wherein the auxiliary anionic surfactant comprises an ethoxylated $C_{12}$–$C_{22}$ alkyl sulfate.

11. A composition according to claim 1 which additionally comprises from about 0.1% to about 20% by weight of an auxiliary nonionic surfactant selected from $C_{12}$–$C_{14}$ fatty acid mono-and diethanolamides and polyhydroxy fatty acid amide surfactants.

12. A composition according to claim 1 wherein the zwitterionic surfactant is selected from alkyl betaine, amido betaine, alkyl sultaine and mixtures thereof.

13. A composition according to claim 1 comprising a mixture of auxiliary anionic with zwitterionic or amphoteric surfactants and wherein the level of the individual anionic, zwitterionic and amphoteric surfactant components is in the range from about 1% to 15% by weight.

14. A composition according to claim 1 wherein the weight ratio of auxiliary anionic surfactant: zwitterionic and/or amphoteric surfactant is in the range of from about 1:2 to about 6:1.

15. A composition according to claim 1 wherein the auxiliary anionic, zwitterionic and amphoteric surfactants together comprise from about 8% to about 35%.

16. A composition according to claim 1 comprising from about 0.1% to about 20% by weight of nonionic surfactant selected from ethoxylated oils or fats having the formula (XII)

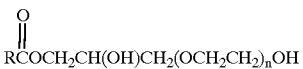

wherein n is from about 5 to 200, preferably from about 20 to about 100, more preferably from about 30 to about 85, and wherein R comprises an aliphatic radical having an average from about 5 to 20 carbon atoms, preferably from about 9 to 20 atoms, more preferably from about 11 to 18 carbon atoms, most preferably from about 12 to 16 carbon atoms.

17. A composition according to claim 1 additionally comprising up to about 20% by weight of perfume or cosmetic oil.

18. A composition according to claim 1 additionally comprising moisturiser selected from sodium pyrrolidone carboxylic acid, L-proline and mixtures thereof.

* * * * *

UNITED STATES PATENT AND TRADEMARK OFFICE
CERTIFICATE OF CORRECTION

PATENT NO. : 6,074,996
DATED : June 13, 2000
INVENTOR(S) : R. P. Elliott et al.

It is certified that error appears in the above-identified patent and that said Letters Patent is hereby corrected as shown below:

Column 14,
Line 64, "or" should read -- of --.

Column 15,
Line 7, "homopolymercan" should read -- homopolymers and --.
Line 35, "formula" should read -- formula [III] --.
Line 48, "formula" should read -- formula [IV] --.
Line 57, "formula" should read -- formula [V] --.
Line 63, "formula" should read -- formula [VI] --.

Signed and Sealed this

Twelfth Day of March, 2002

*Attest:*

JAMES E. ROGAN
*Attesting Officer*   *Director of the United States Patent and Trademark Office*